(12) United States Patent
Matzik et al.

(10) Patent No.: US 6,569,211 B2
(45) Date of Patent: May 27, 2003

(54) 5,6-DIHYDROXYINDOLINES AS ADDITIVES FOR HAIR DYEING PREPARATIONS

(75) Inventors: Iduna Matzik, Erkrath (DE); Detlef Hollenberg, Erkrath (DE); Mechthild Borgerding, Langenfeld (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/975,921

(22) Filed: Oct. 12, 2001

(65) Prior Publication Data

US 2002/0032938 A1 Mar. 21, 2002

Related U.S. Application Data

(63) Continuation of application No. 08/459,378, filed on Jun. 2, 1995, now abandoned, which is a continuation of application No. 08/244,164, filed as application No. PCT/EP92/02578 on Nov. 10, 1992, now abandoned.

(30) Foreign Application Priority Data

Nov. 19, 1991 (DE) .......................................... 41 37 971

(51) Int. Cl.$^7$ ................................................. A61K 7/13
(52) U.S. Cl. .................................. 8/409; 8/423; 8/406
(58) Field of Search ................................. 8/405–9, 423

(56) References Cited

U.S. PATENT DOCUMENTS

| | | |
|---|---|---|
| 2,934,396 A | 4/1960 | Charle et al. |
| 3,194,734 A | 7/1965 | Seemuller et al. |
| 3,649,160 A * | 3/1972 | Kalopissis et al. |
| 3,993,436 A | 11/1976 | Fujinuma |
| 4,013,404 A | 3/1977 | Parent et al. |
| 4,425,132 A | 1/1984 | Grollier et al. |
| 4,595,765 A | 6/1986 | Murphy |
| 4,750,908 A | 6/1988 | Rosenbaum et al. |
| 4,797,130 A | 1/1989 | Clausen et al. |
| 4,808,190 A | 2/1989 | Grollier et al. |
| 4,822,375 A | 4/1989 | Lang et al. |
| 4,888,027 A | 12/1989 | Grollier et al. |
| 4,921,503 A | 5/1990 | Anderson et al. |
| 4,923,479 A | 5/1990 | Braun |
| 5,011,500 A | 4/1991 | Grollier et al. |
| 5,021,067 A | 6/1991 | Grollier |
| 5,034,015 A | 7/1991 | Junino et al. |
| 5,073,174 A | 12/1991 | Vayssie et al. |
| 5,096,455 A | 3/1992 | Grollier |
| 5,131,911 A | 7/1992 | Lang et al. |
| 5,135,544 A | 8/1992 | Grollier et al. |
| 5,167,669 A | 12/1992 | Grollier |
| 5,178,637 A * | 1/1993 | Lagrange et al. |
| 5,180,396 A | 1/1993 | Grollier et al. |
| 5,180,996 A * | 1/1993 | Grollier et al. |
| 5,190,564 A | 3/1993 | Lang et al. |
| 5,207,798 A | 5/1993 | Cotteret et al. |
| 5,254,135 A | 10/1993 | Lang et al. |
| 5,261,926 A | 11/1993 | Lang et al. |
| 5,279,616 A | 1/1994 | Lang et al. |
| 5,279,617 A | 1/1994 | Prota et al. |
| 5,279,618 A | 1/1994 | Prota et al. |
| 5,279,620 A | 1/1994 | Junino et al. |
| 5,340,366 A | 8/1994 | Lang et al. |
| 5,364,414 A | 11/1994 | Lang et al. |
| 5,391,206 A | 2/1995 | Cotteret |

(List continued on next page.)

FOREIGN PATENT DOCUMENTS

| | | |
|---|---|---|
| DE | 1 916 139 | 11/1969 |
| DE | 197 32 975 | 2/1999 |
| EP | 0 337 853 | 5/1992 |
| EP | 0 530 229 | 6/1995 |
| EP | 0 462 857 | 3/1998 |
| FR | 2 008 797 | 1/1970 |
| GB | 2 033 392 | 5/1980 |
| GB | 2 211 517 | 7/1989 |
| GB | 2 213 169 | 8/1989 |
| JP | 01 233 210 | 9/1989 |
| WO | WO91/17739 | 11/1991 |

OTHER PUBLICATIONS

Mishra, et al., "Studies Related to the Chemistry of Melanins. Part III. Synthesis of 5,6–Dihydroxyindoline", J. Chem. Soc. (c), pp. 1424 to 1427, 1967.

Chavdarian, et al., "Oxidative and Cardiovascular Studies on Natural and Synthetic Cathecholamines," Journal of Medicinal Chemistry, vol. 21, No. 6, pp. 548–554, (p. 553), 1978.

Binns, et al.: "Studies Related to the Chemistry of Melanins. Part XIII. Sutdies on the Structures of Dopamine Melanen", Journal of Chemical Society (C), vol. 15, pp. 2063–2070, (Newcastle upon Tyne, GB), 1979.

Derwent WPI database, Accession No. 1989–314090 [43], abstract of JP 01 233210, Sep. 19, 1989.

*Primary Examiner*—Margaret Einsmann
(74) *Attorney, Agent, or Firm*—Stephen D. Harper; Gregory M. Hill

(57) ABSTRACT

The invention concerns the use of indoline derivatives of formula (I):

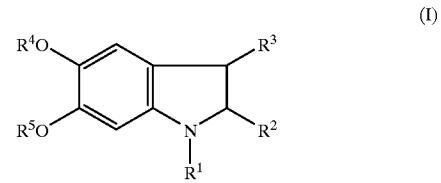

in which $R^1$, $R^2$, $R^3$, $R^4$ and $R^5$ independently of one another represent hydrogen or $C_{1-4}$ alkyl groups, or $R^4$ and $R^5$ together with the oxygen atoms to which they are attached represent a $C_{1-4}$ alkylenedioxy group, or of salts of such indoline derivatives, as additives to hair dyeing agents of the direct dyeing or primary intermediate/secondary intermediate type, thus producing hair dyeing with excellent color fastness characteristics.

16 Claims, No Drawings

U.S. PATENT DOCUMENTS

| | | |
|---|---|---|
| 5,399,713 A | 3/1995 | Knuebel et al. |
| 5,413,612 A | 5/1995 | Wenke |
| 5,425,993 A | 6/1995 | Morancais et al. |
| 5,441,542 A | 8/1995 | Prota et al. |
| 5,478,360 A | 12/1995 | Grollier et al. |
| 5,492,541 A | 2/1996 | Murphy et al. |
| 5,496,543 A | 3/1996 | Lagrange et al. |
| 5,516,916 A | 5/1996 | Murphy et al. |
| 5,518,505 A | 5/1996 | Cotteret |
| 5,534,267 A | 7/1996 | Neunhoeffer et al. |
| 5,538,517 A | 7/1996 | Samain et al. |
| 5,540,738 A | 7/1996 | Chan et al. |
| 5,583,234 A | 12/1996 | Lagrange et al. |
| 5,609,649 A | 3/1997 | Junino et al. |
| 5,609,650 A | 3/1997 | Knuebel et al. |
| 5,611,817 A | 3/1997 | Moeller et al. |
| 5,628,799 A | 5/1997 | Wenke et al. |
| 5,670,099 A | 9/1997 | Morancais et al. |
| 5,683,474 A | 11/1997 | Cotteret et al. |
| 5,743,919 A | 4/1998 | Moeller et al. |
| 5,752,982 A | 5/1998 | Lang et al. |
| 5,776,497 A | 7/1998 | Lagrange et al. |
| 5,938,792 A | 8/1999 | Lang et al. |
| 6,090,160 A | 7/2000 | Junino et al. |
| 6,090,161 A | 7/2000 | Hoeffkes et al. |

* cited by examiner

5,6-DIHYDROXYINDOLINES AS ADDITIVES FOR HAIR DYEING PREPARATIONS

CROSS REFERENCE TO RELATED APPLICATIONS

This application is a continuation of U.S. application Ser. No. 08/459,378 filed on Jun. 2, 1995, now abandoned, which is a continuation of U.S. application Ser. No. 08/244,164 filed on Jun. 17, 1994, now abandoned, which in turn is a national stage application under 35 U.S.C. §371 of international application PCT/EP92/02578 filed on Nov. 10, 1992, the international application not being published in English. This application also claims priority under 35 U.S.C. §119 to DE 41 37 971.3, filed on Nov. 19, 1991.

FIELD OF THE INVENTION

This invention relates to the use of indolines, more particularly 5,6-dihydroxyindolines, as an additive for hair dye formulations based on substantive dyes or on oxidation dye precursors of the primary intermediate and secondary intermediate type.

BACKGROUND OF THE INVENTION

The coloring components in conventional hair dye formulations are generally either substantive dyes or dyes which are formed from oxidation dye precursors of the primary intermediate and secondary intermediate type by oxidation with atmospheric oxygen or with other oxidizing agents (for example $H_2O_2$). For use in hair dye formations, the dyes are incorporated in a cosmetic carrier. The substantive dyes used are, for example, nitrophenylenediamine derivatives, anthraquinone derivatives or naphthoquinone derivatives.

The oxidation dyes used typically consist of a combination of a primary intermediate, for example a primary aromatic amine containing another free or substituted hydroxy or amino group in the para position or the ortho position, diaminopyridines, heterocyclic hydrazone derivatives, 4-aminopyrazolone derivatives or tetraaminopyridines, and a secondary intermediate, for example m-phenylenediamines, 3-aminophenols, resorcinols, naphthols, pyrazolones. These intermediates react in a coupling reaction in the presence of atmospheric oxygen or other oxidizing agents to form the actual dyes.

Good hair dye formulations are required above all to satisfy the following requirements. They must form the required color tone with sufficient intensity. In addition, they must be readily absorbed onto human hair without overly staining the scalp. The colors produced must be highly stable to heat, light, shampoos and the chemicals used for permanent waving. Finally, hair dye formulations must be toxicologically and dermatologically safe.

Accordingly, there is a constant need for hair dye formulations having improved toxicological and performance properties, more particularly in regard to the fastness of the hair colors produced.

It has now surprisingly been found that it is possible to improve the coloring properties of conventional hair dye formulations both of the primary and secondary intermediate type and also those based on substantive dyes.

DETAILED DESCRIPTION OF THE INVENTION

Hair colors distinctly superior to the colors obtained with known hair dye formulations in regard to intensity and fastness can be obtained by using only small quantities of indolines corresponding to formula I:

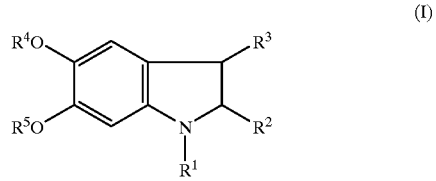

in which $R^1$, $R^2$, $R^3$, $R^4$ and $R^5$ independently of one another represent hydrogen or $C_{1-4}$ alkyl groups, or $R^4$ and $R^5$ together with the oxygen atoms to which they are attached represent a $C_{1-4}$ alkylenedioxy group, or salts thereof as an additive for hair dye formulations containing typical substantive dyes or in hair dye formulations containing oxidation dye precursors of the primary intermediate and secondary intermediate type.

By virtue of the chemical similarity between the indolines of formula I used in accordance with the invention and the basic units of the natural melanin dye present in the hair, the indoline-containing hair dye formulations can also be expected to show favorable toxicological and dermatological behavior.

5,6-Dimethoxyindoline and 5,6-dihydroxyindoline are known from the literature. Their production is described, for example, in *J. Chem. Soc.* (C), 1967, pages 1424 to 1427. The alkyl-substituted indolines corresponding to formula I can be similarly prepared from the correspondingly substituted 5,6-dihydroxyindoles or alkoxyindoles by catalytic hydrogenation. Another process for the production of 5,6-dihydroxyindolines from 5,6-dimethoxyindoles by reduction with sodium cyanoborohydride and elimination of the methoxy groups in concentrated hydrochloric acid is described in *Journal of Medicinal Chemistry*, 1978, Vol. 21, No. 6, page 553.

Indolines corresponding to formula I, in which one of the substituents $R^1$, $R^2$ and $R^3$ is a methyl group and the others are hydrogen atoms, are preferred, the parent compound 5,6-dihydroxyindoline being most particularly preferred.

The indolines to be used in accordance with the invention or salts thereof are added on the one hand to hair dye formulations containing oxidation dye precursors of the primary intermediate and secondary intermediate type, a three-component system consisting of typical primary intermediate, typical secondary intermediate and the indoline derivative being formed. However, there is no need to use only one secondary intermediate and one primary intermediate; rather, mixtures of typical secondary intermediates and mixtures of typical primary intermediates may also be used instead of the individual components. On the other hand, the indolines or salts thereof are added to hair dye formulations containing typical substantive dyes.

The indolines corresponding to formula I to be used in accordance with the invention may be used in free form or in the form of their salts, preferably hydrochlorides, hydrobromides, sulfates, phosphates, acetates, propionates, lactates or citrates.

The present invention also relates to hair dye formulations containing indolines corresponding to formula I or salts thereof and typical primary intermediates and typical secondary intermediates in a carrier and to hair dye formulations containing indolines corresponding to formula I or salts thereof and typical substantive dyes in a carrier.

The indolines corresponding to formula I modify the colors obtained with the conventional hair dye systems mentioned above to the extent that depth of color and fastness are both distinctly improved.

Suitable typical primary and secondary intermediates are any of the known compounds, for example resorcinol, 2-methyl resorcinol, α-naphthol, 1,5-dihydroxynaphthalene, 3-aminophenol, p-amino-o-cresol, 2-chloro-3-amino-6-methylphenol, 2,4-dichloro-3-aminophenol, 1,3-bis-(2,4-diaminophenoxy)-propane, 1-phenyl-3-methyl-5-pyrazolone and 1-phenyl-3-amino-5-pyrazolone as secondary intermediates and p-phenylenediamine, p-tolylenediamine, 2-chloro-p-phenyldiamine, N-methyl-p-phenylenediamine and p-aminophenol, for example, as primary intermediates.

Similarly, the typical substantive dye used may be selected from any of the compounds known for this purpose, for example 2-nitro-p-phenylenediamine, 6-chloro-4-nitro-2-aminophenol, 2-amino-4,6-dinitrophenol, 1-(β-hydroxyethyl)-amino-2-nitro-4-bis-(β-hydroxyethyl)-aminobenzene, 1-(β-hydroxyethyl)-amino-2-nitro-4-aminobenzene, 1-(β-hydroxyethyl)-amino-2-nitrobenzene, 1,4-diamino-5-nitroanthraquinone, 1,4-diaminoanthraquinone, 1,4,5,8-tetraaminoanthraquinone, 1-amino-4-methylaminoanthraquinone.

The primary intermediate and the secondary intermediate are each present in the oxidation hair dye in quantities of 0.05 to 5% by weight and preferably in quantities of 0.1 to 2% by weight, based on the hair dye formulation as a whole. Substantive dyes are present in the formulations based on substantive dyes in a quantity of 0.05 to 5% by weight and preferably in a quantity of 0.1 to 2% by weight, based on the hair dye preparation as a whole. The indolines corresponding to formula I are added in quantities of 0.05 to 5% by weight and preferably in quantities of 0.05 to 2% by weight, based on the hair dye formulation as a whole.

To produce the hair dye formulations according to the invention, the substantive dyes or the oxidation dye precursors of the secondary intermediate and primary intermediate type are incorporated in a suitable cosmetic carrier. Suitable cosmetic carriers are, for example, creams, emulsions, gels or even surfactant-containing foaming solutions, for example shampoos, foam aerosols or other preparations suitable for application to the hair.

Typical constituents of such cosmetic preparations are, for example, wetting agents and emulsifiers, such as anionic, nonionic or ampholytic surfactants, for example fatty alcohol sulfates, alkanesulfonates, α-olefin sulfonates, fatty alcohol polyglycol ether sulfates, ethylene oxide adducts with fatty alcohols, with fatty acids, with alkylphenols, with sorbitan fatty acid esters, with fatty acid partial glycerides and with fatty acid alkanolamides, thickeners such as, for example, fatty alcohols, fatty acids, paraffin oils, fatty acid esters and other fatty components in emulsified form, water-soluble polymeric thickeners such as, for example, methyl or hydroxyethyl cellulose, starch, vegetable gums, water-soluble synthetic polymers, water-soluble biopolymers (for example xanthan gum), hair-care additives such as, for example, water-soluble cationic polymers, protein derivatives, pantothenic acid, vitamins, plant extracts, cholesterol and sugars, electrolyte and buffer salts, pH regulators, complexing agents and perfume oils, reducing agents for stabilizing the dye, for example sodium sulfite or ascorbic acid.

To produce the hair dye formulations according to the invention, the constituents of the cosmetic carrier are incorporated in the usual quantities for this purpose. For example, emulsifiers are used in concentrations of 0.5 to 30% by weight, while thickeners are used in concentrations of 0.1 to 25% by weight, based on the hair dye formulation as a whole.

A particularly suitable carrier is an oil-in-water emulsion containing 1 to 25% by weight of a fatty component and 0.5 to 30% by weight of an emulsifier from the group of anionic, nonionic, ampholytic or zwitterionic surfactants. If the indolines to be used in accordance with the invention are used as an additive for hair dye formulations of the primary intermediate and secondary intermediate type, the primary intermediate and secondary intermediate are each incorporated in the carrier in quantities of 0.05 to 5% by weight and preferably in quantities of 0.1 to 2% by weight, based on the hair dye formulation as a whole, while the indolines corresponding to formula I are incorporated in the carrier in quantities of 0.05 to 5% by weight and preferably in quantities of 0.05 to 2% by weight, based on the hair dye formulation as a whole.

Basically, the hair color may be oxidatively developed with atmospheric oxygen. However, it is preferred to use a chemical oxidizing agent, particularly when the hair is to be lightened as well as colored. Suitable oxidizing agents are, in particular, hydrogen peroxide or adducts thereof with urea, melamine or sodium borate and mixtures of such hydrogen peroxide adducts with potassium peroxydisulfate.

The hair dye formulations according to the invention may be used in a mildly acidic, neutral or alkaline medium, irrespective of their cosmetic presentation, for example as a cream, gel or shampoo. The hair dye formulations are preferably used at a pH in the range from 6 to 10 and at a temperature in the range from 15° C. to 40° C. After a contact time of around 30 minutes, the hair dye formulation is removed from the hair to be dyed by rinsing. The hair is then washed with a mild shampoo and dried. There is no need to wash the hair with a shampoo in cases where a carrier of high surfactant content, for example a dye shampoo, has been used.

The following Examples are intended to illustrate the invention without limiting it in any way.

EXAMPLES

Application Examples 5,6-Dihydroxyindoline as an additive for hair dye formulations of the secondary intermediate and primary intermediate type:

Example 1

|  | Comparison | Invention |
| --- | --- | --- |
| Tallow fatty alcohol | 6.5 g | 6.5 g |
| Coconut oil Lorol | 2.0 g | 2.0 g |
| Lauryl ether sulfate (Texapon ® N 25) | 7.28 g | 7.28 g |
| p-Aminophenol · HCl | 0.44 g | 0.44 g |
| p-Tolylenediamine · HCl | 0.31 g | 0.31 g |
| m-Aminophenol | 0.114 g | 0.114 g |
| p-Amino-o-cresol | 0.11 g | 0.11 g |
| 2-Methylresorcinol | 0.08 g | 0.08 g |
| 5,6-Dihydroxyindoline | — | 0.5 g |
| $Na_2SO_3$ | 0.5 g | 0.5 g |
| $(NH_4)_2SO_4$ | 0.8 g | 0.8 g |

-continued

|  | Comparison | Invention |
|---|---|---|
| Conc. NH₃ solution | to pH = 9.5 | to pH = 9.5 |
| Water | ad 100 g | ad 100 g |

The constituents were mixed together in the above order. After addition of the oxidation dye precursors and the inhibitor, the emulsion was first adjusted to pH 9.5 with concentrated ammonia solution and then made up to 100 g with water.

The color was oxidatively developed with 3% hydrogen peroxide solution as oxidizing agent. To this end, 50 g of hydrogen peroxide solution (3%) were added to and mixed with 100 g of the emulsion.

The dye cream was applied to approximately 5 cm long strands of standardized, 90% gray, but not especially pretreated human hair and left thereon for 30 minutes at 27° C. On completion of the dyeing process, the hair was rinsed, washed with a typical shampoo and then dried.

Hair dye formulation 1 according to the invention produced a red-brown color with a very good gray-masking effect and very good fastness to washing. After washing 6 times with a commercial shampoo, 95% of the color was still in place as opposed to 62% where the comparison hair dye formulation 1 was used.

Example 2

|  | Comparison | Invention |
|---|---|---|
| Tallow fatty alcohol | 6.5 g | 6.5 g |
| Coconut oil Lorol | 2.0 g | 2.0 g |
| Lauryl ether sulfate (Texapon ® N 25) | 7.28 g | 7.28 g |
| p-Aminophenol | 0.3 g | 0.3 g |
| p-Tolylenediamine | 0.02 g | 0.02 g |
| p-Amino-o-cresol | 0.05 g | 0.05 g |
| 5,6-Dihydroxyindoline | — | 0.3 g |
| Na₂SO₃ | 0.5 g | 0.5 g |
| (NH₄)₂SO₄ | 1.0 g | 1.0 g |
| Conc. NH₃ solution | to pH = 9.5 | to pH = 9.5 |
| Water | ad 100 g | ad 100 g |

The hair dye formulations were applied in the same way as in Example 1.

Hair dye formulation 2 according to the invention produced a golden blond color with very good fastness to washing. After washing 6 times, 92% of the color was still in place as opposed to 65% where comparison hair dye formulation 2 was used.

Example 3

|  | Comparison | Invention |
|---|---|---|
| Tallow fatty alcohol | 6.5 g | 6.5 g |
| Coconut oil Lorol | 2.0 g | 2.0 g |
| Lauryl ether sulfate (Texapon ® N 25) | 7.28 g | 7.28 g |
| p-Aminophenol | 0.14 g | 0.14 g |
| p-Tolylenediamine | 1.10 g | 1.10 g |
| Resorcinol | 0.08 g | 0.08 g |

-continued

|  | Comparison | Invention |
|---|---|---|
| 2-Methylresorcinol | 0.105 g | 0.105 g |
| 2,4-Dichloro-3-aminophenol · HCl | 0.04 g | 0.04 g |
| 5,6-Dihydroxyindoline | — | 0.5 g |
| Na₂SO₃ | 0.5 g | 0.5 g |
| (NH₄)₂SO₄ | 0.8 g | 0.8 g |
| Conc. NH₃ solution | to pH = 9.5 | to pH = 9.5 |
| Water | ad 100 g | ad 100 g |

The hair dye formulations were applied in the same way as in Examples 1 and 2.

Hair dye formulation 3 according to the invention produced a dark brown color with a 100% gray-masking effect and good fastness to washing. After washing 6 times, 96% of the color was still in place as opposed to 78% where comparison hair dye formulation 3 was used.

5,6-Dihydroxyindoline as an additive for hair dye formulations based on substantive dyes.

Example 4

|  | Comparison | Invention |
|---|---|---|
| Tallow fatty alcohol | 4.0 g | 4.0 g |
| Coconut oil Lorol | 1.0 g | 1.0 g |
| Eumulgin B1 | 2.0 g | 2.0 g |
| 1-(β-hydroxyethyl)-amino-2-nitro-4-bis-(β-hydroxyethyl)-aminobenzene | 1.0 g | 1.0 g |
| 1-(β-hydroxyethyl)-amino-2-nitro-4-aminobenzene | 0.1 g | 0.1 g |
| 1-(β-hydroxyethyl)-amino-2-nitrobenzene | 0.2 g | 0.2 g |
| 5,6-Dihydroxyindoline | — | 0.2 g |
| Water | ad 100 g | ad 100 g |

Comparison hair dye formulations and the hair dye formulation according to the invention were applied to 5 cm long strands of standardized, 90% gray, but not especially pretreated human hair and left thereon for about 20 minutes at 27° C., washed with a typical shampoo, rinsed with water and dried. Hair dye formulation 4 according to the invention produced a mid-brown color with a good gray-masking effect and good fastness to washing. After washing 6 times, 75% of the color was still in place as opposed to 40% where comparison hair dye formulation 4 was used.

What is claimed is:
1. A method of dyeing hair comprising

(a) forming a hair dye composition comprising
   (i) at least one oxidative primary intermediate dye precursor,
   (ii) at least one oxidative secondary intermediate dye precursor; and
   (iii) at least one indoline compound corresponding to formula I or a salt thereof

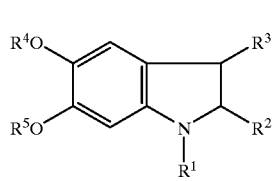

(I)

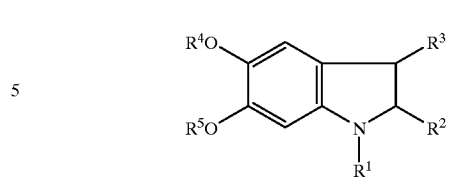

(I)

wherein R¹, R², R³, R⁴ and R⁵ independently of one another represent hydrogen or a $C_{1-4}$ alkyl group, or R⁴ and R⁵ together with the oxygen atoms to which they are attached represent a $C_{1-4}$ alkylenedioxy group, wherein the oxidative primary intermediate dye precursor is different from the indoline compound of formula I; and (b) applying the dye composition to hair.

2. The method of claim 1 wherein R¹, R², R³, R⁴ and R⁵ are hydrogen, or wherein one of R¹, R² or R³ is a methyl group and the remaining R substituents are hydrogen.

3. The method of claim 2 wherein the indoline compound comprises 5,6-dihydroxyindoline.

4. The method of claim 1 wherein R¹ is a $C_{1-4}$ alkyl group.

5. The method of claim 1 wherein the hair dye composition further comprises at least one substantive dye.

6. The method of claim 1 wherein the primary intermediate, the secondary intermediate, and the indoline compound are each present in the composition in an amount of 0.05 weight percent to 5 weight percent, based on the total weight of the composition.

7. The method of claim 1 wherein prior to the applying step, at least one oxidation agent is added to the hair dye composition.

8. The method of claim 7, wherein the oxidizing agent comprises hydrogen peroxide, or adducts of hydrogen peroxide with urea, melamine, or sodium borate.

9. A composition for coloring hair comprising:

(a) a cosmetic carrier;

(b) from 0.05 weight percent to 5 weight percent, based on the total weight of the composition, of at least one oxidative primary intermediate dye precursor;

(c) from 0.05 weight percent to 5 weight percent, based on the total weight of the composition, of at least one oxidative secondary intermediate dye precursor, and (d) from 0.05 weight percent to 5 weight percent, based on the total weight of the composition, of at least one indoline compound corresponding to formula I or a salt thereof wherein R¹, R², R³, R⁴ and R⁵ independently of one another represent hydrogen or a $C_{1-4}$ alkyl group, or R⁴ and R⁵ together with the oxygen atoms to which they are attached represent a $C_{1-4}$ alkylenedioxy group, wherein the oxidative primary intermediate dye precursor is different from the indoline compound of formula I.

10. The composition of claim 9 wherein R¹, R², R³, R⁴ and R⁵ are hydrogen, or wherein one of R¹, R² or R³ is a methyl group and the remaining R substituents are hydrogen.

11. The composition of claim 10 wherein the indoline compound comprises 5,6-dihydroxyindoline.

12. The composition of claim 9 wherein R¹ is a $C_{1-4}$ alkyl group.

13. The composition of claim 9 wherein the hair dye composition further comprises from 0.05 weight percent to 5 weight percent of at least one substantive dye, based on the total weight of the composition.

14. The composition of claim 9 wherein the primary intermediate, the secondary intermediate, and the indoline compound are each present in the composition in an amount of 0.1 weight percent to 2 weight percent, based on the total weight of the composition.

15. The composition of claim 9 wherein the secondary intermediate comprises at least one compound selected from 2-methyl resorcinol, α-naphthol, 1,5-dihydroxynaphthalene, 3-aminophenol, p-amino-o-cresol, 2-chloro-3-amino-6-methylphenol, 2,4-dichloro-3-aminophenol, 1,3-bis-(2,4-diaminophenoxy)-propane, 1-phenyl-3-methyl-5-pyrazolone, or 1-phenyl-3-amino-5-pyrazolone, or combinations thereof; and the primary intermediate comprises at least one compound selected from p-phenylenediamine, p-tolylenediamine, 2-chloro-p-phenyldiamine, N-methyl-p-phenylenediamine, or p-aminophenol, or combinations thereof.

16. The method of claim 1 wherein the hair dye composition has improved color fastness relative to a hair dye composition not containing the indoline compound of formula I.

* * * * *